United States Patent [19]

Nickels et al.

[11] Patent Number: 4,705,869
[45] Date of Patent: Nov. 10, 1987

[54] PREPARATION OF FATTY ACID ESTERS OF ASCORBIC ACID

[75] Inventors: Helmut Nickels, Mutterstadt; Alfred Hackenberger, Ludwigshafen, both of Fed. Rep. of Germany

[73] Assignee: BASF Aktiengesellschaft, Ludwigshafen, Fed. Rep. of Germany

[21] Appl. No.: 762,031

[22] Filed: Aug. 2, 1985

Related U.S. Application Data

[63] Continuation of Ser. No. 587,115, Mar. 7, 1984, abandoned.

[30] Foreign Application Priority Data

Mar. 12, 1983 [DE] Fed. Rep. of Germany ....... 3308922

[51] Int. Cl.$^4$ .......................................... C07D 307/62
[52] U.S. Cl. .................................................. 549/317
[58] Field of Search .......................................... 549/317

[56] References Cited

U.S. PATENT DOCUMENTS 2,350,435  9/1981  Wells et al. ......................... 549/317
4,151,178  4/1979  Seib et al. ............................ 549/317
4,289,702  9/1981  Gruetsmacher et al. ........... 549/317

FOREIGN PATENT DOCUMENTS 639776  12/1936  Fed. Rep. of Germany .
2743526  4/1978  Fed. Rep. of Germany .
418324  8/1966  Switzerland .
1013946  12/1965  United Kingdom .

OTHER PUBLICATIONS

R. C. Causins et al., Jour. Am. Oil Chem. Soc., vol. 54(7), Jul. 1977, pp. 308–312.
German Abstract of Belgian Pat. No. 611,648.

*Primary Examiner*—Norma S. Milestone
*Attorney, Agent, or Firm*—Oblon, Fisher, Spivak, McClelland & Maier

[57] ABSTRACT

Fatty acid esters of ascorbic acid are prepared by a process in which a homogeneous mixture of
(a) ascorbic acid,
(c) concentrated sulfuric acid having a concentration of not less than 96% and
(c) a methyl or ethyl ester of a fatty acid of 12 to 18 carbon atoms
is reacted at from 20° to 50° C.

Using the novel process, the fatty acid esters of ascorbic acid, in particular ascorbyl palmitate, which are very desirable antioxidants are obtained by a procedure which is technically simpler and hence cheaper than the conventional processes, but in equally good yields.

14 Claims, No Drawings

PREPARATION OF FATTY ACID ESTERS OF ASCORBIC ACID

This application is a continuation of application Ser. No. 587,115, filed Mar. 7, 1984, and now abandoned.

The present invention relates to an improved process for the preparation of fatty acid esters of ascorbic acid.

Fatty acid esters of ascorbic acid, such as the esters of palmitic acid, of myristic acid and of stearic acid, are known to the important, effective antioxidants for foods which have a very high fat content. There has therefore been no lack of attempts to develop a very advantageous process for the preparation of these esters.

For example, U.S. Pat. No. 2,350,435 discloses a process for the preparation of 6-O-fatty acid esters of ascorbic acid, in which excess ascorbic acid is reacted with higher saturated aliphatic fatty acids in 95% strength sulfuric acid. Since the ascorbic acid is normally the most expensive starting compound, and the excess ascorbic acid cannot be readily recovered from the reaction mixture after the reaction, this process has not proven very suitable industrially in respect of the yields based on ascorbic acid.

To improve the yields of fatty acid esters of ascorbic acid, German Laid-Open Application DOS No. 2,743,526 (U.S. Pat. No. 4,151,178) therefore recommends carrying out the reaction in not less than about 96, preferably 98–99, % strength sulfuric acid, and moreover using the fatty acids (instead of the ascorbic acid) in a molar excess and maintaining the reactants within certain concentration ranges. Using this process, it is possible to obtain the desired fatty acid esters in yields as high as 85% of theory.

However, the use of an excess of fatty acids, which is required to achieve the good yields, entails substantial disadvantages. Because of their tendency to form an emulsion, fatty acids make the working up more difficult to carry out. It is not possible simply to filter off the ascorbic acid esters; instead, they have to be extracted from the reaction mixture, and only certain solvents, eg. ethers, are suitable for this extractive working up procedure. The solvent has to be used in an amount corresponding to 20–30 times the initial volume of sulfuric acid. Furthermore, careful washing with sodium chloride solution has to be carried out in order to avoid emulsions.

The process described in German Laid-Open Application DOS No. 2,854,353 gives high yields of 6-O-ascorbates in spite of the fact that equimolar amounts of ascorbic acid and fatty acids are used. However, the disadvantage of this process is that anhydrous hydrogen fluoride is required as the reaction medium.

It is an object of the present invention to provide a process for the preparation of fatty acid esters of ascorbic acid, in which the desired ascorbic acid esters are obtained in good yields in a very simple manner, even without the use of an excess of ascorbic acid or of fatty acid, and without the use of hydrogen fluoride as the reaction medium, this being difficult industrially.

We have found that this object is achieved, and that, surprisingly, the above disadvantages of the conventional processes can be avoided, if, for the preparation of the ascorbic acid esters, the ascorbic acid is reacted, in more than about 96% strength sulfuric acid, with the methyl or ethyl ester of the appropriate fatty acid, instead of with the fatty acid itself.

Although the reaction of fatty acid esters with ascorbic acid for the preparation of antioxidants is disclosed in Belgian Pat. No. 611,648, heating the stated starting materials to 90°–120° C. by the method described in this patent results only in a complicated product mixture.

In contrast, reacting a roughly equimolar mixture of fatty acid alkyl esters and ascorbic acid in highly concentrated sulfuric acid surprisingly gives 6-O-fatty acid esters of ascorbic acid in yields as good as those obtained when a 36% excess of fatty acid is used.

The present invention accordingly relates to a process for the preparation of fatty acid esters of ascorbic acid, wherein a homogeneous mixture of
(a) ascorbic acid,
(b) concentrated sulfuric acid having a concentration of not less than about 96%, and
(c) a methyl or ethyl ester of a fatty acid of 12 to 18 carbon atoms
is reacted at from 20° to 50° C.

The term ascorbic acid refers to all isomers of ascorbic acid, such as L-ascorbic acid and D-isoascorbic acid. The natural isomer, ie. L-ascorbic acid, is preferably used.

The fatty acid esters used are preferably those of lauric acid, palmitic acid, myristic acid or stearic acid, in particular their methyl esters.

The concentration of the sulfuric acid should be higher than 96%, the best yields being achieved with about 100% strength sulfuric acid.

The reaction is preferably carried out at room temperature, and the reaction times are generally about 10–25 hours.

The ascorbic acid and the fatty acid ester are advantageously used in about equimolar amounts. Because an excess of fatty acids in the reaction mixture has been dispensed with, the latter is substantially simpler to work up.

The reaction according to the invention is advantageously carried out as follows: the ascorbic acid is dissolved in the concentrated sulfuric acid at room temperature, the fatty acid ester is added, stirring is continued for a few minutes, and the reaction mixture is then left to stand at room temperature.

The reaction mixture is worked up by pouring it onto ice water. The ascorbic acid ester crystallizes out and can simply be filtered off. The extraction, including working up of the extracts by distillation, which is required in the conventional processes and is very expensive industrially can be dispensed with. After drying, the filtration residue can be recrystallized from a suitable solvent.

German Laid-Open Application DOS No. 2,743,526 states that, in addition to an excess of fatty acid, a limited concentration range for the reactants is an important precondition for good yields. The molar ratio of the fatty acid and the ascorbic acid together to the sulfuric acid should be from 0.1 to 0.3, preferably from 0.15 to 0.17. In the case of palmitic acid, which is particularly important commercially, the upper limit is about 0.15 at room temperature, for reasons of solubility. The same authors mention, in J. Am. Oil chem. Soc. 54 (1977), 308, that when palmitic acid is used in an excess of 36% in 99% strength sulfuric acid at 20° C., the highest possible ascorbic acid concentration is 1.25 moles/liter (corresponding to a molar ratio of 0.15). The molar ratio of, for example, palmitic acid which is stated in the preferred examples of the abovementioned German Laid- Open Application No. is 0.125, corresponding to an ascorbic acid concentration of 1 mole/liter.

In contrast, the lower alkyl esters of the fatty acids have a substantially better solubility than the fatty acids themselves in sulfuric acid, so that, in the reaction according to the invention, the ascorbic acid concentration in the reaction mixture can be increased. Moreover, we have found that ascorbic acid concentrations higher than about 1.3 moles/liter, with equivalent amounts of palmitates, can give yields as high as 85%. In the novel reaction with palmitates, the ascorbic acid concentration can be increased to as high as about 2 moles/liter. As a result, the amount of sulfuric acid required for the reaction is substantially decreased; this further simplifies the working up step.

Using the novel process, the fatty acid esters of ascorbic acid, in particular ascorbyl palmitate, which are very desirable antioxidants are obtained in a technically simpler and hence cheaper manner but in equally good yields.

EXAMPLES 1 TO 3

Portions of 3.5 g (0.02 mole) of L-ascorbic acid were dissolved in 15 ml (0.28 mole) of 100% strength sulfuric acid at room temperature, and 5.4 g (0.02 mole) of methyl palmitate or 5.68 g (0.02 mole) of ethyl palmitate in liquid form were added to this solution all at once. The reaction mixture was then stirred for a few minutes, after which it was left to stand at room temperature for the time shown in Table 1. It was then poured onto ice water and filtered. The filtration residue was washed acid-free with water, dried and then recrystallized. Table 1 shows the concentrations, present in each case in the reaction mixture, of ascorbic acid and of the palmitate, and the reaction times and the yields obtained.

TABLE 1

| Example | Ascorbic acid [mole/liter] | Palmitate [mole/liter] | Time [hours] | Yield [%] |
|---|---|---|---|---|
| 1 | 1.32 | 1.32(*) | 20 | 80.2 |
| 2 | 1.32 | 1.32(*) | 24 | 85.1 |
| 3 | 1.32 | 1.32(**) | 24 | 78 |

(*)Methyl palmitate
(**)Ethyl palmitate

COMPARATIVE EXAMPLES 1 TO 3

Portions of 3.5 g (0.02 mole) of L-ascorbic acid were dissolved in 20 ml (0.37 mole) of 100% strength sulfuric acid at room temperature, and 5.13 g (0.02 mole) or 6.9 g (0.027 mole) of palmitic acid were added to this solution. The reaction mixture was stirred until it was homogeneous, about 1–2 hours being required to achieve this; it was then left to stand at room temperature.

When the reaction time shown in Table 2 had elapsed, the reaction mixture was poured onto about 300 ml of ice water and then worked up by extraction, using a procedure similar to that described in German Laid-Open Application DOS No. 2,743,526.

Table 2 shows the concentrations, present in each case in the reaction mixture, of ascorbic acid and of palmitic acid, and the reaction times and the yields obtained.

TABLE 2

| Comparative Example | Ascorbic acid [mole/liter] | Palmitic acid [mole/liter] | Time [hours] | Yield [%] |
|---|---|---|---|---|
| 1 | 0.99 | 0.99 | 20 | 66.3 |
| 2 | 0.99 | 0.99 | 24 | 72.3 |
| 3 | 0.99 | 1.34 | 36 | 85 |

EXAMPLES 4 TO 6

L-Ascorbic acid in 100% strength sulfuric acid was reacted with equimolar amounts of methyl laurate, methyl myristate and methyl stearate by a method similar to that described in Examples 1 to 3. Table 3 shows the concentrations, present in each case in the reaction mixture, of ascorbic acid and of the fatty acid methyl ester, and the reaction times and the yields obtained.

The following fatty acid methyl esters were used:

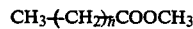

methyl laurate (n=10)
methyl myristate (n=12)
and methyl stearate (n=16).

TABLE 3

| Example | Ester [n] | Ascorbic acid [mole/liter] | Methyl ester [mole/liter] | Time [hours] | Yield [%] |
|---|---|---|---|---|---|
| 4* | 10 | 1.66 | 1.66 | 24 | 90.6* |
| 5 | 12 | 1.66 | 1.66 | 24 | 75.1 |
| 6 | 16 | 1.33 | 1.33 | 30 | 70.0 |

*For comparison: According to U.S. Pat. No. 4,151,178, a yield of only 86% of theory was obtained, in spite of the fact that a 36% excess of lauric acid was used.

We claim:

1. A process for the preparation of a fatty acid ester of ascorbic acid, wherein a homogeneous mixture of:
   (a) ascorbic acid;
   (b) concentrated sulfuric acid having a concentration higher than 96%; and
   (c) a methyl ester, an ethyl ester or a mixture thereof of a saturated fatty acid of 12 to 18 carbon atoms;
   is reacted at a temperature of from 20° to 50° C.

2. The process of claim 1, wherein a methyl ester of the said fatty acid is used.

3. The process of claim 1, wherein an ethyl ester of the said fatty acid is used.

4. The process of claim 1, wherein the ascorbic acid comprises L-ascorbic acid.

5. The process of claim 1, wherein the ascorbic acid comprises D-isoascorbic acid.

6. The process of claim 1, wherein the fatty acid is at least one member selected from the group consisting of lauric acid, palmitic acid, myristic acid, stearic acid and a mixture thereof.

7. The process of claim 1, wherein the concentrated sulfuric acid has a concentration of about 100%.

8. The process of claim 1, wherein the reaction is carried out at room temperature.

9. The process of claim 1, wherein the reaction is run for 10 to 25 hours.

10. The process of claim 1, wherein methyl palmitate is used.

11. The process of claim 1, wherein ethyl palmitate is used.

12. The process of claim 1, wherein methyl laurate is used.

13. The process of claim 1, wherein methyl myristate is used.

14. The process of claim 1, wherein methyl stearate is used.

* * * * *